US012773410B2

(12) United States Patent
Yadla et al.

(10) Patent No.: US 12,773,410 B2
(45) Date of Patent: Oct. 27, 2026

(54) EGFR INHIBITOR FOR THE TREATMENT OF HEAD AND NECK CANCER

(71) Applicant: NATCO PHARMA LIMITED, Hyderabad (IN)

(72) Inventors: Sheshu Babu Yadla, Hyderabad (IN); Praveen Chowdary Myneni, Hyderabad (IN); Venkata Ramana Gogula, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 328 days.

(21) Appl. No.: 18/568,160

(22) PCT Filed: Jun. 9, 2022

(86) PCT No.: PCT/GB2022/051450

§ 371 (c)(1),
(2) Date: Dec. 7, 2023

(87) PCT Pub. No.: WO2022/258977

PCT Pub. Date: Dec. 15, 2022

(65) Prior Publication Data

US 2024/0285642 A1 Aug. 29, 2024

(30) Foreign Application Priority Data

Jun. 10, 2021 (GB) ..................................... 2108300
Jun. 10, 2021 (GB) ..................................... 2108302

(51) Int. Cl.

| | |
|---|---|
| ***A61K 31/5377*** | (2006.01) |
| ***A61K 31/282*** | (2006.01) |
| ***A61K 31/337*** | (2006.01) |
| ***A61K 33/243*** | (2019.01) |
| ***A61P 35/04*** | (2006.01) |

(52) U.S. Cl.

CPC ........ *A61K 31/5377* (2013.01); *A61K 31/282* (2013.01); *A61K 31/337* (2013.01); *A61K 33/243* (2019.01); *A61P 35/04* (2018.01)

(58) Field of Classification Search

CPC .............. A61K 31/5377; A61K 31/282; A61K 31/337; A61K 31/555; A61K 33/243; A61P 35/00; A61P 35/04

See application file for complete search history.

(56) References Cited

U.S. PATENT DOCUMENTS

| | | | |
|---|---|---|---|
| 8,143,250 | B2 | 3/2012 | Jyothi Prasad et al. |
| 8,921,362 | B2 | 12/2014 | Adibhatla Kali Satya et al. |
| 9,050,341 | B2 | 6/2015 | Abidhatla Kali Satya et al. |
| 9,481,655 | B2 | 11/2016 | Adibhatla Kali Satya et al. |
| 2019/0201408 | A1 | 7/2019 | Adibhatla Kali Satya et al. |
| 2021/0196719 | A1 | 7/2021 | Zhang et al. |

FOREIGN PATENT DOCUMENTS

| | | | |
|---|---|---|---|
| CN | 117545476 | B | 3/2025 |
| EP | 2229369 | B1 | 9/2010 |
| EP | 4337191 | B1 | 12/2024 |
| JP | 7579465 | B2 | 11/2024 |
| KR | 102713072 | B1 | 10/2024 |
| WO | 2001034574 | A1 | 5/2001 |
| WO | 2009090661 | A1 | 7/2009 |
| WO | 2011021212 | A1 | 2/2011 |
| WO | 2019223716 | A1 | 11/2019 |
| WO | 2020177678 | A1 | 9/2020 |
| WO | 2022258977 | A1 | 12/2022 |

OTHER PUBLICATIONS

Parkinson, Tanya et al., "An Inhibitor of the epidermal growth factor receptor function does not affect the ability of human papillomavirus 11 to form warts in the xenografted immunodeficient mouse model", Science Direct, Antiviral Research, 74, (2007), 43-50.

Eisenhauer, E. A. et al., "New response evaluation criteria in solid tumours: revised RECIST guideline (version 1.1)", Science Direct, European Journal of Cancer 45, (2009), 228-247.

Burtness, Barbara et al., "Pembrolizumab alone or with chemotherapy versus cetuximab with chemotherapy for recurrent or metastatic squamous cell carcinoma of the head and neck (keynote-048): a randomised, open-lable, phase 3 study", The Lancet, 2019, 394 (10212), 1915-1928.

Vermorken, Jan B. et al., "Platinum-Based Chemotherapy plus Cetuximab in Head and Neck Cancer", The New England Journal of Medicine, 2008, 359, 1116-27.

Muratori, Leonardo, "Target Therapies in recurrent or metastatic head and neck cancer: state of the art and novel perspectives. A systematic review", Crit Rev Oncol Hematol. Jul. 2019:139:41-52.

Klein, Jonah D. et al., "Antitumor effect of vandetanib through EGFR inhibition in head and neck squamous cell carcinoma", Head Neck. 2012; 34(9):1269-76.

Abhold, Eric L. et al., "EGFR Kinase Promotes Acquisition of stem cell-like properties: a potential therapeutic target in head and neck squamous cell carcinoma stem cells", Plos One, Feb. 2012, vol. 7, Issue 2, 1-8.

Moyer, James D. et al., "Induction of Apoptosis and cell cycle arrest by CP-358, 774, an inhibitor of epidermal growth factor receptor tyrosine kinase", Cancer Res. 1997; 57(21):4838-48.

(Continued)

*Primary Examiner* — Sarah Pihonak
(74) *Attorney, Agent, or Firm* — Dickinson Wright PLLC

(57) ABSTRACT

The invention relates to the treatment of recurrent and/or metastatic squamous cell carcinoma of the head and neck (preferably recurrent squamous cell carcinoma of the head and neck) with a compound which is (3-ethynyl-phenyl)-[7-methoxy-6-(3-morpholin-4-yl-propoxy)-quinazolin-4-yl]-amine (NRC-2694) or a pharmaceutically acceptable salt thereof. The invention also relates to the treatment of head and neck cancer with a compound which is (3-ethynyl-phenyl)-[7-methoxy-6-(3-morpholin-4-yl-propoxy)-quinazolin-4-yl]-amine (NRC-2694) or a pharmaceutically acceptable salt thereof, wherein the treating the head and neck cancer comprises reducing the size of one or more tumours associated with the head and neck cancer.

27 Claims, 1 Drawing Sheet

(56) References Cited

OTHER PUBLICATIONS

Gullick W. J., "Prevalence of aberrant expression of the epidermal growth factor receptor in human cancers", British Medical Bulletin, 1991, vol. 47, No. 1, 87-98.
National Comprehensive Cancer Network (NCCN) Clinical Practice Guidelines in Oncology, Poland Edition, Head and Neck Cancers, Version 2.2022—Nov. 3, 2022.
National Comprehensive Cancer Network (NCCN) Clinical Practice Guidelines in Oncology, Poland Edition, Head and Neck Cancers, Version 2.2020, vol. 18, Issue 7, Jul. 2020.
Common Terminology Criteria for Adverse Events (CTCAE), U.S. Department of Health and Human Services, Nov. 27, 2017, 1-155.
Aichler, Michaela et al., "Epidermal growth factor receptor (EGFR) is an independent adverse prognostic factor in esophageal adenocarcinoma patients treated with cisplatin-based neoadjuvant chemotherapy", Impact Journals, Oncotarget, 2014, vol. 5, No. 16, 6620-6632.
Liu, Ya-Ping et al., "Molecular mechanisms of chemo-and radiotheraphy resistance and the potential implications for cancer treatment", MedComm (2020). 2021; 2(3):315-340.
Chibaudel, Benoist et al., "Induction theraphy with cetuximab plus docetaxel, cisplatin, and 5-fluorouracil (ETPF) in patients with resectable nonmetastatic stage III or IV squamous cell carcinoma of the oropharynx. A Gercor phase II ECHO-07 study", Cancer Medicine, 2015, 4(5), 721-731.
Marsha-Kay, N.D. et al., "Radiation resistance in head and neck squamous cell carcinoma:dire need for an appropriate sensitizer", Oncogene. 2020; 39(18):3638-3649.
Kirby et al., "Gefitinib (ZD1839, Iressa™) as palliative treatment in recurrent or metastatic head and neck cancer," British journal of cancer 2006, 94(5), 631-636.

EGFR INHIBITOR FOR THE TREATMENT OF HEAD AND NECK CANCER

FIELD OF THE INVENTION

The present invention relates to the treatment of cancer of the head and neck.

BACKGROUND OF THE INVENTION

Significant progress has been made in the treatment of solid tumours in the last few years. However, many forms of cancer remain incurable and are resistant to standard treatments. Head and neck cancer is a very recalcitrant cancer and treatment options are limited. A particularly recalcitrant cancer is recurrent squamous cell carcinoma of the head and neck. This cancer has a high mortality rate, a high morbidity rate (particularly through reduction of the ability to speak and swallow) and there is no successful treatment.

Head and neck cancer and recurrent and/or metastatic squamous cell carcinoma of the head and neck (particularly where the recurrent and/or metastatic squamous cell carcinoma of the head and neck is recurrent squamous cell carcinoma of the head and neck) are hard to treat for a number of reasons. The cancer is infiltrative and multifocal and this can prevent effective resection. Cancer of the head and neck and recurrent and/or metastatic squamous cell carcinoma of the head and neck (particularly where the recurrent and/or metastatic squamous cell carcinoma of the head and neck is recurrent squamous cell carcinoma of the head and neck) can also be resistant to standard therapies.

(3-Ethynyl-phenyl)-[7-methoxy-6-(3-morpholin-4-yl-propoxy)-quinazolin-4-yl]-amine (NRC-2694) is an epidermal growth factor receptor (EGFR) tyrosine kinase inhibitor. The structure of NRC-2694 is shown below.

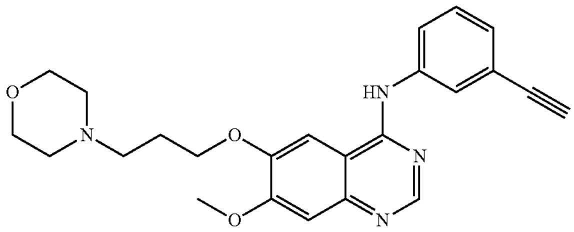 [SMILES: C#Cc1cccc(Nc2ncnc3cc(OC)c(OCCCN4CCOCC4)cc23)c1]

NRC-2694 has been found to be effective in certain cancer types (WO 2009/090661 A1 and WO 2011/021212 A1). NRC-2694 has also been found to cause low to moderate inhibition of growth of a head and neck cancer cell line grafted into athymic female mice (Parkinson et al, Antiviral Research 74 (2007) 43-50).

NRC-2694 may be administered as NRC-2694 dihydrochloride (known as NRC-2694-A)

The efficacy of specific therapeutic agents against different cancers is unpredictable. Kinase inhibitors active against some cancers have been found to be inactive against other cancer types. There remains a need to identify an active agent which is effective in treating cancer of the head and neck, and in particular an agent which is capable of causing tumour regression and reducing tumour size. Reduction in tumour size is particularly important in head and neck cancer, as it is likely to make it easier for the patient to speak and swallow. There also remains a need to identify an active agent which is effective in treating recurrent squamous cell carcinoma of the head and neck.

SUMMARY OF THE INVENTION

It has been found that NRC-2694 is an effective treatment for head and neck cancer and for squamous cell carcinoma of the head and neck. NRC-2694 is able to reduce the size of the tumours associated with cancer of the head and neck and improve outcomes for patients. This is an important advance in the treatment of head and neck cancer. NRC-2694 is also able to inhibit tumour growth and/or reduce the size of the tumours associated with squamous cell carcinoma of the head and neck and improve outcomes for patients. This is an important advance in the treatment of squamous cell carcinoma of the head and neck, a cancer with a high mortality rate and few effective treatment options.

The invention accordingly provides a compound for use in the treatment of recurrent and/or metastatic squamous cell carcinoma of the head and neck (R/M HNSCC) in a patient, wherein the compound is (3-ethynyl-phenyl)-[7-methoxy-6-(3-morpholin-4-yl-propoxy)-quinazolin-4-yl]-amine (NRC-2694) or a pharmaceutically acceptable salt thereof. Preferably, the recurrent and/or metastatic squamous cell carcinoma of the head and neck is recurrent squamous cell carcinoma of the head and neck.

The invention accordingly further provides a compound for use in treating head and neck cancer in a patient, wherein: the compound is (3-ethynyl-phenyl)-[7-methoxy-6-(3-morpholin-4-yl-propoxy)-quinazolin-4-yl]-amine (NRC-2694) or a pharmaceutically acceptable salt thereof; and treating the head and neck cancer comprises reducing the size of one or more tumours associated with the head and neck cancer.

BRIEF DESCRIPTION OF THE TABLES

Figure 1:
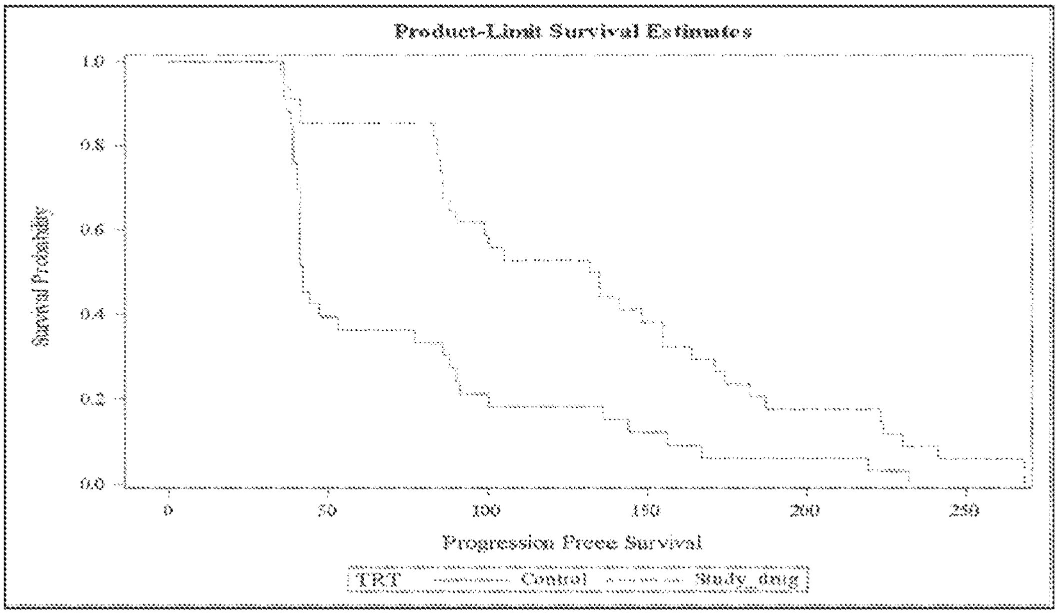
FIG. 1 shows Kaplan-Meier estimates of progression free survival.

Table 1 provides a summary of tumour evaluation for five patients with recurrent squamous cell carcinoma of the head and neck as discussed in Example 1.

Table 2 provides the patient demographics in the study of Example 2.

Table 3 provides progression free survival (PFS) data for the study of Example 2.

Table 4 provides objective response rate (ORR) data for the study of Example 2.

DETAILED DESCRIPTION OF THE INVENTION

NRC-2694 has the systematic name (3-ethynyl-phenyl)-[7-methoxy-6-(3-morpholin-4-yl-propoxy)-quinazolin-4-yl]-amine. NRC-2694 may also be referred to as N-(3-ethynylphenyl)-7-methoxy-6-[3-(4-morpholinyl)propoxy)-4-quinazolinamine. NRC-2694 and salts thereof may be produced by standard synthetic techniques. A synthesis of NRC-2694 is described in WO 2011/021212 A1.

The compound is NRC-2694 or a pharmaceutically acceptable salt thereof. The pharmaceutically acceptable salt is typically a pharmaceutically acceptable acid addition salt.

Typically, the compound is a hydrochloride salt of NRC-2694. For instance, the compound may be the monohydrochloride of NRC-2694 (NRC-2694-B) or the dihydrochloride of NRC-2694 (NRC-2694-A). Preferably, the compound is NRC-2694 dihydrochloride (NRC-2694-A).

The cancer treated is a head and neck cancer. The head and neck cancer may be carcinoma or the head and neck, lymphoma of the head and neck, adenocarcinoma of the head and neck, or sarcoma of the head and neck. Typically the cancer is carcinoma of the head and neck.

The cancer treated may for instance be a squamous cell carcinoma of the head and neck. Other forms of cancer of the head and neck include lymphoma of the head and neck, adenocarcinoma of the head and neck, and sarcoma of the head and neck.

The cancer treated may be a recurrent and/or metastatic cancer, and in particular recurrent and/or metastatic squamous cell carcinoma of the head and neck. As such, the squamous cell carcinoma of the head and neck may be a squamous cell carcinoma of the head and neck that has recurred and/or metastasised following treatment of a previous instance of squamous cell carcinoma of the head and neck in the patient. Preferably, the cancer treated may be a recurrent cancer, and in particular recurrent squamous cell carcinoma of the head and neck. As such, the squamous cell carcinoma of the head and neck may be a squamous cell carcinoma of the head and neck that has recurred following treatment of a previous instance of squamous cell carcinoma of the head and neck in the patient. Typically, a recurrent tumour or lesion has developed within ten years after the completion of treatment to remove, destroy or reduce in size earlier tumours or lesions. For instance, the patient may have previously suffered from squamous cell carcinoma of the head and neck within a period of ten years, a period of five years, or a period of two years, before initiation of treatment for the recurrent squamous cell carcinoma of the head and neck with the compound.

The recurrent squamous cell carcinoma of the head and neck may be squamous cell carcinoma of the head and neck which has recurred following previous treatment for squamous cell carcinoma of the head and neck. For instance, the patient may have previously been treated for squamous cell carcinoma of the head and neck with an EGFR inhibitor (for instance erlotinib, gefitinib, lapatinib, cetuximab or vandetanib, preferably cetuximab), with an immunotherapy (for instance pembrolizumab or nivolumab), with a tumour-agnostic therapy (for instance larotrectinib) or with a chemotherapy (for instance 5-fluorouracil, gemcitabine, cisplatin, carboplatin, paclitaxel or docetaxel).

For instance, the patient may have previously been treated for head and neck cancer (e.g. squamous cell carcinoma of the head and neck) with cetuximab, pembrolizumab or nivolumab. The patient may have previously been treated for head and neck cancer or squamous cell carcinoma of the head and neck with radiotherapy or surgery. The patient may have previously been treated with chemotherapy, for instance chemotherapy with paclitaxel in combination with cisplatin or carboplatin.

Patients having head and neck cancer (e.g. recurrent squamous cell carcinoma of the head and neck) typically have one or more tumours (lesions or carcinomas) in the head and neck. The patient may have one or more tumours selected from a laryngeal tumour, a hypopharyngeal tumour, a tumour of the nasal cavity, a tumour of the paranasal sinus, a nasopharyngeal tumour, an oral tumour, an oropharyngeal tumour, and a tumour of the salivary gland. The patient may have laryngeal cancer, hypopharyngeal cancer, nasal cavity cancer, paranasal sinus cancer, nasopharyngeal cancer, oral cancer, oropharyngeal cancer, or salivary gland cancer.

The head and neck cancer may be metastatic cancer For instance, the head and neck cancer may be metastatic recurrent squamous cell carcinoma of the head and neck. The head and neck cancer may have metastasised to the lymph nodes, the lung, the brain, the liver or the bones or any other organ of the human body.

The head and neck cancer may be at any stage. The head and neck cancer may be stage I, stage II, stage III or stage IV cancer. For instance, the head and neck cancer may be stage III or stage IV cancer.

The recurrent squamous cell carcinoma of the head and neck may be metastatic recurrent squamous cell carcinoma of the head and neck. The recurrent squamous cell carcinoma of the head and neck may have metastasised to the lymph nodes, the lung, the brain, the liver or the bones or any other organ of the human body.

The recurrent squamous cell carcinoma of the head and neck may be at any stage. The recurrent squamous cell carcinoma of the head and neck may be stage I, stage II, stage III or stage IV cancer. For instance, the recurrent squamous cell carcinoma of the head and neck may be stage III or stage IV cancer.

Treating the head and neck cancer may comprise reducing the size of one or more tumours associated with the head and neck cancer. As such, the treatment may cause tumour regression in the head and neck cancer. Treating the head and neck cancer may comprise reducing the number of tumours or lesions present in the head and neck of the patient. Treating the head and neck cancer may further include alleviating, ameliorating or preventing aggravation of the symptoms of the head and neck cancer. Treating head and neck cancer may further comprise reducing progression of the head and neck cancer. Treating head and neck cancer may further comprise preventing metastasis of the head and neck cancer. Treating the head and neck cancer may comprise reducing the size of a tumour associated with metastasis of the head and neck cancer.

Treating recurrent and/or metastatic squamous cell carcinoma of the head and neck may include alleviating, ameliorating or preventing aggravation of the symptoms of recurrent and/or metastatic squamous cell carcinoma of the head and neck. Treating recurrent squamous cell carcinoma of the head and neck may include alleviating, ameliorating or preventing aggravation of the symptoms of recurrent squamous cell carcinoma of the head and neck. Typically, treating recurrent squamous cell carcinoma of the head and neck comprises reducing progression of recurrent squamous cell carcinoma of the head and neck. Treating recurrent squamous cell carcinoma of the head and neck may comprise preventing or inhibiting growth of a tumour associated with the recurrent squamous cell carcinoma of the head and neck or reducing the size of a tumour associated with the recurrent squamous cell carcinoma of the head and neck. Treating recurrent squamous cell carcinoma of the head and neck may comprise preventing metastasis of the recurrent squamous cell carcinoma of the head and neck. Preferably, treating recurrent squamous cell carcinoma of the head and neck comprises reducing the size of a tumour associated with the recurrent squamous cell carcinoma of the head and neck. As such, the treatment may cause tumour regression in recurrent squamous cell carcinoma of the head and neck. Treating recurrent squamous cell carcinoma of the head and neck may comprise reducing the number of tumours or lesions present in the head and neck of the patient. Treating recurrent squamous cell carcinoma of the head and neck may comprise reducing the size of a tumour associated with metastasis of the recurrent squamous cell carcinoma of the head and neck.

When the treatment reduces the size of a tumour associated with the head and neck cancer or the recurrent and/or metastatic squamous cell carcinoma of the head and neck (wherein, preferably, the recurrent and/or metastatic squamous cell carcinoma of the head and neck is recurrent squamous cell carcinoma of the head and neck), the size of the tumour is typically reduced from base line by at least 10%. Base line is the size of the tumour on or before the date treatment with the compound is first started. For instance, the base line may be the size of the tumour as measured by a CT, MRI or PET scan before the treatment is first started (for instance within two weeks before treatment is first started). The size of the tumour is typically as measured in accordance with version 1.1 of the RECIST criteria (for instance as described in Eisenhauer et al, European Journal of Cancer 45 (2009) 228-247). Thus, the size of the tumour may decrease by at least 10 mm.

The response to the treatment with the compound may be complete response, partial response or stable disease, in accordance with version 1.1 of the RECIST criteria. Preferably, the response is partial response or complete response. Complete response may comprise disappearance of all target lesions. Partial response may comprise at least a 30% decrease in the sum of diameters of target lesions.

The treatment may achieve progression free survival for at least 45 days, at least 60 days, at least 120 days or at least 180 days.

The reduction in tumour size may be greater 20%, greater than 30% or greater than 50% reduction relative to base line. The reduction in tumour size may be observed after 30 days of treatment, after 45 days of treatment, or after 60 days of treatment.

The compound may be effective in treating head and neck cancer in patients where other treatments have not been successful. The head and neck cancer may therefore be head and neck cancer which is resistant to radiotherapy and/or chemotherapy. For instance, the patient may have previously been subject to radiotherapy or chemotherapy for treatment of the head and neck cancer and the response to the radiotherapy or chemotherapy may have been no response or stable disease.

The compound has been found to be effective in treating recurrent squamous cell carcinoma of the head and neck in patients where other treatments have not been successful. The recurrent squamous cell carcinoma of the head and neck may therefore be recurrent squamous cell carcinoma of the head and neck which is resistant to radiotherapy and/or chemotherapy. For instance, the patient may have previously been subject to radiotherapy or chemotherapy for treatment of the recurrent squamous cell carcinoma of the head and neck and the response to the radiotherapy or chemotherapy may have been no response or stable disease.

The head and neck cancer may be resistant to treatment with erlotinib and/or gefitinib. The recurrent squamous cell carcinoma of the head and neck may be resistant to treatment with erlotinib and/or gefitinib.

The treatment may reduce multidrug resistance, for instance during chemotherapy. For instance, the treatment may reduce resistance to cisplatin, carboplatin or paclitaxel.

The patient may have received at least one line of cancer therapy prior to treatment with the compound. The patient may have received at least two lines of cancer therapy prior to treatment with the compound. The lines of cancer therapy may be selected from treatment with an EGFR inhibitor other than NRC-2694 (for instance erlotinib, gefitinib, lapatinib, cetuximab or vandetanib, preferably cetuximab), treatment with an immunotherapy (for instance pembrolizumab or nivolumab), treatment with a tumour-agnostic therapy (for instance larotrectinib) and treatment with a chemotherapy (for instance gemcitabine, 5-fluorouracil, cisplatin, carboplatin, paclitaxel or docetaxel).

The patient may have had a diagnosis of head and neck cancer for greater than six months, greater than one year, greater than two years or greater than three years. The patient may have had a diagnosis of recurrent and/or metastatic squamous cell carcinoma of the head and neck for greater than one month, greater that six months, greater than one year, greater than two years or greater than three years. In particular, the patient may have had a diagnosis of recurrent squamous cell carcinoma of the head and neck for greater than one month, greater than six months, greater than one year, greater than two years or greater than three years.

The patient is typically a human patient. The patient may be male or female. The age of the patient is typically at least 18 years, for instance from 30 to 70 years or from 40 to 60 years.

The compound may be administered in a variety of dosage forms. The compound can be administered orally, for example as a tablet, a capsule, a troche, a lozenge, an aqueous or oily suspension, a dispersible powder or as granules. The compound may alternatively be administered parenterally, for instance subcutaneously, intravenously, intramuscularly, intrasternally, transdermally or by infusion. The compound may also be administered as a suppository.

The compound is typically administered orally. The compound is preferably administered in the form of a tablet.

The compound is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, lauryl sulphates; and, in general, non-toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be a syrup, an emulsion or a suspension. The syrup may contain as carrier, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. A suspension or solution for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compound may be administered to the patient as many times as required to treat the head and neck cancer or the recurrent and/or metastatic squamous cell carcinoma of the head and neck (where, preferably, the recurrent and/or metastatic squamous cell carcinoma of the head and neck is recurrent squamous cell carcinoma of the head and neck). The compound may be administered once or twice weekly, or once, twice, three times or four times daily. Typically, the compound is administered to the patient once or twice daily. Preferably, the compound is administered to the patient once daily.

A therapeutically effective amount of the compound is administered to the patient. A typical dose is from 1 mg/day to 1000 mg/day, according to the age and weight of the patient to be treated, the severity of the recurrent squamous cell carcinoma of the head and neck and the frequency and route of administration. Typically, the compound is administered to a human patient in a dose of from 50 mg/day to 500 mg/day. Preferably, the compound is administered to the patient in a dose of from 100 mg/day to 400 mg/day. For instance, the daily dose may be from 75 mg/day to 125 mg/day, from 125 mg/day to 175 mg/day, from 175 mg/day to 225 mg/day, from 225 mg/day to 275 mg/day, from 275 mg/day to 325 mg/day, from 325 mg/day to 375 mg/day, from 375 mg/day to 425 mg/day, or from 425 mg/day to 475 mg/day. The daily dose may be about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day or about 500 mg/day. The compound may be administered to a human patient under fasted or fed conditions. The compound may be administered to a human patient with or without regard to food.

The compound may be administered to the patient in a dose of from 200 mg/day to 400 mg/day. The compound may be administered to the patient in a dose of from 250 mg/day to 350 mg/day. Preferably, the compound is administered to the patient in a dose of from 275 mg/day to 325 mg/day. For instance, around 300 mg of the compound may be administered per day. The compound may be administered in one or more doses per day. Typically, the compound is administered to the patient in an amount of from 275 mg to 325 mg as a single dose once per day. The compound may be administered once per day for at least 5 days, for instance once per day for from 1 month to 6 months.

The compound may be administered as a monotherapy. Alternatively, the compound may be administered as part of a combination therapy, for instance together with radiotherapy, immunotherapy (for instance pembrolizumab or nivolumab), tumour-agnostic therapy (for instance larotrectinib), chemotherapy (for instance 5-fluorouracil, gemcitabine, cisplatin, carboplatin, paclitaxel or docetaxel) or a combination thereof. The compound may be administered as part of a combination therapy with chemotherapy, for instance as part of a combination therapy with one or more of 5-fluorouracil, gemcitabine, cisplatin, carboplatin, paclitaxel and docetaxel. The chemotherapy may comprise administration of one or more of cisplatin, carboplatin and paclitaxel. The compound may for instance be administered in combination with (a) cisplatin and paclitaxel or (b) carboplatin and paclitaxel.

The combination therapy may comprise simultaneous or separate administration of the two treatments. For instance, the patient may be undergoing chemotherapy at the time the compound is administered. The chemotherapy may for instance be administered separately to treatment with the compound, for instance once every two to five weeks.

The invention accordingly provides a compound for use in a treatment defined herein in combination with chemotherapy. The compound may be for use in the treatment defined herein in combination with (a) cisplatin and paclitaxel or (b) carboplatin and paclitaxel. The invention also provides chemotherapy for use in a treatment defined herein in combination with the compound. Also provided is a product comprising (i) the compound and (ii) cisplatin and paclitaxel or carboplatin and paclitaxel, for use in the simultaneous, sequential or separate treatment of a disease defined herein. The patient may be undergoing chemotherapy with (a) cisplatin and paclitaxel or (b) carboplatin and paclitaxel when the compound is administered.

The cisplatin or carboplatin may be administered at a dose of 25 $mg/m^2$ to 175 $mg/m^2$ of total body surface area, for instance from 75 $mg/m^2$ to 125 $mg/m^2$ of total body surface area. The paclitaxel may be administered at a dose of 100 $mg/m^2$ to 250 $mg/m^2$ of total body surface area, for instance from 150 $mg/m^2$ to 200 $mg/m^2$ of total body surface area.

The invention also provides a method for treating head and neck cancer in a patient, the method comprising administering a compound to the patient, which compound is (3-ethynyl-phenyl)-[7-methoxy-6-(3-morpholin-4-yl-propoxy)-quinazolin-4-yl]-amine (NRC-2694) or a pharmaceutically acceptable salt thereof, wherein treating the head and neck cancer comprises reducing the size of one or more tumours associated with the head and neck cancer. The invention also provides use of a compound in the manufacture of a medicament for the treatment of head and neck cancer in a patient, which compound is (3-ethynyl-phenyl)-[7-methoxy-6-(3-morpholin-4-yl-propoxy)-quinazolin-4-yl]-amine (NRC-2694) or a pharmaceutically acceptable salt thereof, and wherein treating the head and neck cancer comprises reducing the size of one or more tumours associated with the head and neck cancer. The cancer, the patient, the compound and the treatment may be as defined herein for the compound for use according to the invention.

The invention also provides a method for treating recurrent and/or metastatic squamous cell carcinoma of the head and neck in a patient, the method comprising administering a compound to the patient, which compound is (3-ethynyl-phenyl)-[7-methoxy-6-(3-morpholin-4-yl-propoxy)-quinazolin-4-yl]-amine (NRC-2694) or a pharmaceutically acceptable salt thereof. In particular, the invention also provides a method for treating recurrent squamous cell carcinoma of the head and neck in a patient, the method comprising administering a compound to the patient, which compound is (3-ethynyl-phenyl)-[7-methoxy-6-(3-morpholin-4-yl-propoxy)-quinazolin-4-yl]-amine (NRC-2694) or a pharmaceutically acceptable salt thereof. The invention also provides use of a compound in the manufacture of a medicament for the treatment of recurrent and/or metastatic squamous cell carcinoma of the head and neck in a patient, which compound is (3-ethynyl-phenyl)-[7-methoxy-6-(3-morpholin-4-yl-propoxy)-quinazolin-4-yl]-amine (NRC-2694) or a pharmaceutically acceptable salt thereof. In particular, the invention also provides use of a compound in the manufacture of a medicament for the treatment of recurrent squamous cell carcinoma of the head and neck in a patient, which compound is (3-ethynyl-phenyl)-[7-methoxy-6-(3-morpholin-4-yl-propoxy)-quinazolin-4-yl]-amine (NRC-2694) or a pharmaceutically acceptable salt thereof. The carcinoma, the patient, the compound and the treatment may be as defined herein for the compound for use according to the invention.

The invention is described in more detail by the following example, which is not intended to limit the scope of the claims.

EXAMPLES

Example 1

Summary

A Phase I clinical study was conducted to evaluate the safety, pharmacokinetics and anti-tumour activity of NRC-2694-A (NRC-2694 dihydrochloride) in patients with recurrent squamous cell carcinoma of the head and neck.

Objectives

Primary: To determine the maximum tolerated dose (MTD) and Dose Limiting Toxicity (DLT) of NRC-2694-A given orally once daily.

Secondary: To evaluate the single and multiple dose pharmacokinetics and anti-tumour activity of NRC-2694-A.

Study Population

Patients with confirmed diagnosis of advanced solid malignancies for whom standard options do not exist.

Eligibility Criteria

The inclusion criteria were as follows.

- Patients were≥18 years old with expected life expectancy≥8 weeks.
- ECOG Performance Score was less than or equal to 2.
- Adequate bone marrow reserve (WBC at least 3,000/$mm^3$, neutrophil count≥2000/$mm^3$, platelet count≥1, 00,000 $mm^3$ and hemoglobin level 8.0 g/dL), renal function (normal serum creatinine), liver function [total bilirubin level≤2 times upper normal limit (UNL) and serum transaminases levels≤2.5 times UNL/≤5 times for liver metastasis and/or obstructive jaundice. Subjects must have tested negative for, HIV, HbsAg and pregnancy (for female subjects).
- Patients who had not received chemotherapy within 14 days (6 weeks for nitrosoureas or mytomycin C) and radiotherapy within 3 weeks and who had not undergone surgery within 2 weeks before dosing.
- Patients were willing to practice birth control measures during and for 2 months after treatment.

The exclusion criteria were as follows.

- Patients with major illness including active cardiac, hepatic, endocrine, renal or psychiatric disorders inadequately controlled with current therapy.
- Patients with brain metastases or primary CNS malignancies.
- Concurrent therapy for the cancer (Radiation therapy, chemotherapy etc.)
- Patients who were pregnant or lactating
- Any condition, including the presence of laboratory abnormalities, which placed the subject at unacceptable risk if he/she were to participate in the study, and which may obscure the evaluation of toxicity or altered drug metabolism
- Impairment of gastrointestinal function that could significantly alter the absorption of the study drug and also the use of medication altering gastric pH; (mild antacids were permitted if taken either 4 hours before or after the study drug administration)

Study Design

An open label, prospective, non-randomized, multicentre, dose escalation study was performed. The starting dose selected for this study was 100 mg/day and the maximum dose received was 500 mg/day. Eligible subjects were housed in a unit of the hospital for 12 days, beyond which patients who tolerated the drug were treated on out-patient (ambulatory) basis.

Outcome Evaluation

Safety: Assessments were performed within 7 days before administration of study medication and subsequently on Days 12, 18, 24, 30, 45, 60, 75 and 90. However, for assessing the DLT and MTD first 30 day safety data was considered.

Pharmacokinetic Evaluation: Estimation of NRC-2694 in plasma was done using a validated LC-MS/MS method. Based on the plasma concentration data, non-compartmental pharmacokinetic variables viz. area under the curve (AUC), peak plasma concentration ($C_{max}$), time to peak plasma concentration ($T_{max}$), and elimination rate constant, volume of distribution, half-life and clearance were calculated for single dose (on Day 1) as well as at steady state (on Day 12). Blood samples at pre-dose, 0.5, 1, 1.5, 2, 2.5, 3, 4, 6, 8, 12 and 24 hrs were collected in $K_2$ EDTA prefilled vacutainers.

Tumour Evaluation: Change in the size of evaluable tumour from base line was evaluated as per RECIST criteria (version 1.1).

Results

The summary of tumour evaluation for five patients with recurrent squamous cell carcinoma of the head and neck is shown in Table 1.

TABLE 1

| Subject No. | Diagnosis | No. of Days completed | Outcome |
|---|---|---|---|
| 0202 | Head and Neck | 120 | Stable Disease |
| 0207 | Head and Neck | 79 | Stable Disease |
| 0211 | Head and Neck | 120 | Stable Disease |
| 0212 | Head and Neck | 120 | Partial Response |
| 0216 | Head and Neck | 120 | Stable Disease |

Four patients with recurrent squamous cell carcinoma of the head and neck completed 120 days of the trial. A partial response with reduction in tumour size in accordance with the RECIST criteria was observed in one patient (tumour regression). The remaining patients showed stable disease.

Pharmacokinetic data showed dose dependent increase in the concentration from 100 mg/day to 500 mg/day for both Day-1 and Day-12 concentrations.

Conclusion

Once daily administration of NRC-2694-A showed a tolerable safety profile. Dose proportional relationship with respect to pharmacokinetics was observed with NRC-2694-A. The MTD of NRC-2694-A was 400 mg/day. NRC-2694-A demonstrated good objective response and caused tumour size reduction or tumour size stasis in patients with recurrent squamous cell carcinoma of the head and neck.

Example 2

A Phase II clinical study was conducted to evaluate the efficacy and safety of NRC-2694-A in patients with recurrent head and neck squamous cell carcinoma.

Background Information

Head and neck cancers begin in the squamous cells that line the moist, mucosal surfaces inside the head and neck regions (for example, inside the mouth, the nose, and the throat). It is estimated that about 66,470 new cases of oral cavity, pharyngeal or Laryngeal cancers occur annually, which account for about 3.5% of new cancer cases in the United States. An estimated 15,050 deaths from Head and Neck (H&N) cancers may occur during the same period. Squamous cell carcinoma or a variant is the histopathologic type in more than 90% of these tumors.

NRC-2694-A is an organic small molecule having IUPAC name, N-(3-ethynylphenyl)-7-methoxy-6-(3-morpholino-propoxy) quinazolin-4-amine dihydrochloride. It is an orally administered tyrosine kinase inhibitor belonging to the quinazoline class of EGFR inhibitors. Amplified EGFR signaling is frequently found in human tumors and can be caused by various mechanisms. As amplified EGFR signaling plays an important role in carcinogenesis, inhibiting this process is a rational approach in the development of a new chemical entity for treatment of such malignancies.

Study Objectives

Primary objective: The primary objective was to evaluate the efficacy of NRC-2694-A in combination with platinum plus paclitaxel regimen compared to platinum plus paclitaxel regimen alone in terms of progression free survival (PFS) in patients with recurrent and/or metastatic squamous cell carcinoma of the head and neck (R/M HNSCC).

Secondary objectives: The secondary objective was (a) to compare the objective response rate in patients with R/M HNSCC treated with NRC-2694-A in combination with platinum plus paclitaxel regimen compared to platinum plus paclitaxel regimen alone and (b) to compare the safety and tolerability of the two regimens.

Methodology

The study was an open-label, prospective, randomized, active controlled, multicentric phase-II study of NRC-2694-A in patients with histologically/cytologically confirmed HNSCC with radiological progression (recurrence and/or metastasis).

Patients between 18 and 65 years of age with life expectancy≥3 months having recurrent and/or metastatic disease for whom cisplatin/carboplatin plus paclitaxel regimen was planned were eligible for the study. Those who fit all the inclusion and exclusion criteria were randomized to receive either chemotherapy+NRC-2694-A (study drug arm) or chemotherapy alone (control arm).

Arm-I (study drug arm): NRC-2694-A+cisplatin/carboplatin and paclitaxel

Arm-II (control arm): cisplatin/carboplatin and paclitaxel

During the study, 300 mg NRC-2694-A was administered once daily in the morning with or without food with 240 ml of water. The dose of cisplatin was 100 $mg/m^2$ of body surface area as intravenous infusion over an hour. Alternatively, the dose of carboplatin was based on the target area under the curve (AUC) equivalent to 5 mg/mL/min, as an infusion over 1 hour. The choice of platinum compound was per the investigator's discretion and was dependent on the type of platinum received during prior therapy, avoiding repetition. Paclitaxel was given at a dose of 175 $mg/m^2$ of body surface area as an infusion over 3 hours.

Monotherapy: After completion of 6 cycles of chemotherapy in control arm or in study drug arm, patients received 300 mg of NRC-2694-A once daily as a monotherapy.

Eligibility Criteria

Inclusion Criteria:

1. Patients between 18 and 65 years of age with life expectancy≥3 months having recurrent and/or metastatic disease for whom cisplatin/carboplatin plus paclitaxel regimen was planned. This was also in palliative setting.
2. ECOG (Eastern Co-operative Oncology Group) Performance Status≤2.
3. Histologically confirmed squamous cell carcinoma of the head and neck. Primary sites include oral cavity, oropharynx, nasopharynx, hypopharynx, larynx, and paranasal sinus.
4. Adequate bone marrow reserve (WBC (white blood cells) at least 3,000/$mm^3$, neutrophil count≥2000/$mm^3$, platelet count≥1,00,000/$mm^3$ and hemoglobin level 8.0 g/dL), renal function (normal serum creatinine), liver function [total bilirubin level≤2 times upper normal limit (UNL) and serum transaminases levels≤2.5 times UNL/≤5 times for liver metastasis and/or obstructive jaundice].
5. Patients have not received chemotherapy within 30 days (6 weeks for nitrosoureas or mytomycin C) and radiotherapy within 3 weeks and have not undergone surgery within 2 weeks before dosing.
6. Measurable lesion as per Revised RECIST criteria (version 1.1).
7. Patients who received primary radiation therapy were eligible if the locoregional recurrence was in the field of radiation and occurred at least 6 months after therapy completion. If the recurrence was outside the field of radiation, the patient was eligible at least 3 months after therapy completion.
8. Willing to practice birth control during and for 2 months after treatment.
9. Patients who tested negative for HIV, HBsAg, HCV and pregnancy (for female subjects).

Exclusion Criteria:

1. Patients with major illness including active cardiac, hepatic, endocrine, renal or psychiatric disorders inadequately controlled with current therapy.
2. Patients with brain metastases or primary CNS (central nervous system) malignancies. Radiological evaluation of brain metastasis was performed only if the patient has symptoms.
3. Prior EGFR-targeting therapies, prior investigational agents for recurrent or metastatic disease, other concurrent investigational agents, other concurrent anti-cancer treatment.

Criteria for Evaluation

Efficacy Evaluation:

Tumor response was assessed by CT or MRI at baseline and at end of every 6-weeks duration (before start of the next cycle) after the start of treatment until disease progression.

Progression free survival was considered as time from the date of randomization to the date of progression or to the date of death, whichever occurs first.

Disease progression was evaluated per RECIST version 1.1 criteria.2

Objective Response Rate was considered as percentage of patients in each arm achieving complete or partial response to the treatment.

Complete Response (CR): Disappearance of all target lesions.

Partial Response (PR): At least a 30% decrease in the sum of diameters of target lesions.

Safety Evaluation:

Adverse events were monitored throughout the study. Grading of the adverse events was done by NCI CTCAE Version 5.0 (Nov. 27, 2017).

Results

A total of 90 patients were enrolled in the study. Of these patients, 45 patients were in Arm-I (NRC-2694-A+chemotherapy) and 45 patients were in Arm-II (chemotherapy only). Of the 45 patients in Arm-I, 40 patients were male and 5 patients were female with a median age of 50 years (31-66). Of the 45 patients in Arm-II, 41 patients were male and 4 patients were female with a median age of 51 years (30-64). The mean height and weight of patients in Arm-I at pre-dose were 164.0 cm (±7.36) and 51.0 kg (±9.32) respectively. The mean height and weight of patients in Arm-II at pre-dose were 167.0 cm (±7.69) and 53.2 kg (±9.7) respectively. The details of patient demographics are listed in Table 2. Patients with ECOG performance status less than or equal to 2 and fulfilling the eligibility criteria were enrolled. Of the 90 patients enrolled, 67 patients, who completed at least 2 cycles of chemotherapy or one radiological evaluation, were considered for response evaluation. Among these 67 patients, 34 patients were in Arm-I and 33 patients were in Arm-II.

TABLE 2

Patient Demographics

| | Arm-I [NRC-2694-A + chemotherapy] (n = 45) | Arm-II [chemotherapy only] (n = 45) |
|---|---|---|
| Median age in years (range) | 50.0 (31-66) | 51.0 (30-64) |
| Female, n (%) | 5 (11%) | 4 (9%) |
| Male, n (%) | 40 (89%) | 41 (91%) |
| Height in cm (SD) | 164.0 (±7.36) | 167.0 (±7.69) |
| Weight in kg (SD) | 51.0 (±9.32) | 53.2 (±9.7) |

Efficacy Evaluation: Progression-Free Survival (PFS)

The median progression-free survival (PFS) was found to be 4.38 months in patients in Arm-I and 1.38 months in Arm-II (hazard ratio for PFS, 0.436; 95% CI, 0.264-0.722; $p<0.0007$). Inclusion of NRC-2694-A to paclitaxel and platinum chemotherapy regimen was associated with significant increase in the duration of PFS (Table 3). Kaplan-Meier estimates of progression free survival according to treatment group are displayed in FIG. 1.

TABLE 3

Progression free survival (PFS)

| Parameter | Arm-I [NRC-2694-A + chemotherapy] (n = 34) | Arm-II [chemotherapy only] (n = 33) |
|---|---|---|
| Median PFS | 4.38 months (133 Days) | 1.38 months (42 Days) |
| Hazard Ratio (p value at 5% level of significance) | 0.436<br>0.0007 | |
| 95% Confidence Interval | 0.264-0.722 | |

Efficacy Evaluation: Objective Response Rate (ORR)

Inclusion of NRC-2694-A to the chemotherapy regimen significantly increased the ORR of patients in Arm-I compared to those in Arm-II. Complete responses were observed in 5 patients in Arm-I compared to 2 patients in Arm-II. Partial responses were observed in 12 patients in Arm-I as opposed to 5 patients in Arm-II. The ORR observed in Arm-1 was 50%, whereas it was 21% in Arm-II with a p-value of 0.016 (Table 4).

TABLE 4

Objective Response Rate (ORR)

| Parameter | Arm-I [NRC-2694-A + chemotherapy] (n = 34) | Arm-II [chemotherapy only] (n = 33) |
|---|---|---|
| ORR (CR + PR), n (%) | 17 (50) | 7 (21) |
| CR, n | 5 | 2 |
| PR, n | 12 | 5 |
| Odds ratio (p value at 5% level of significance) | 2.71 (0.016) | |

Efficacy Evaluation: Patients Transferred from Chemotherapy-Only Arm to NRC-2694-A Plus Chemotherapy Arm The study protocol allowed patients, who had disease progression in Arm-II (chemotherapy-only Arm) after two cycles of chemotherapy, to receive NRC-2694-A, in addition to the chemotherapy. Seven such patients, who progressed in Arm-II after two cycles, received NRC-2694-A and chemotherapy subsequently. Among these patients, two patients achieved complete response, while two others had stable disease, one patient had progressive disease. This indicates that patients who did not respond to chemotherapy and thus had disease progression, demonstrated complete response after the inclusion of NRC-2694-A.

Efficacy Evaluation: Patients Continued to Stage-II (Monotherapy)

Also, 11 patients who completed Stage-I treatment [Arm-I (9 Patients) and Arm-II (2 Patients)] continued to Stage-II (monotherapy). Of the 9 patients from Arm-I, 2 had complete response, 4 had partial response, 2 had stable disease and 1 patient had progressive disease at the beginning of monotherapy.

During Stage-II, complete response was maintained in 2 patients. Among the 4 patients who had partial response in Stage-I, one patient continued to have partial response, while 2 had stable disease and 1 had progressive disease. Two patients with stable disease in Stage-I continued to have stable disease. However, 1 patient who had progressive disease in Stage-I, continued to have progressive disease.

It is noteworthy that the 2 patients from Arm-II who had partial response and stable disease earlier, achieved complete response in Stage-II. This indicates that NRC-2694-A has therapeutic benefit not only when given in combination with chemotherapy, but also when given as a monotherapy.

Figure 2:
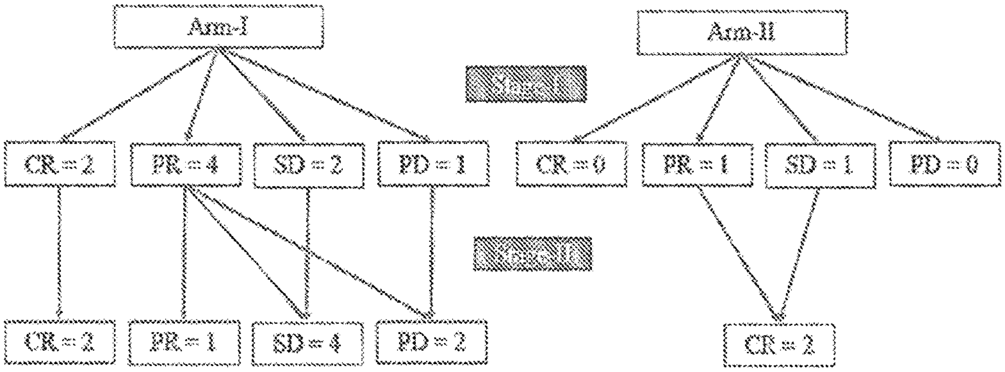
FIG. 2 shows efficacy results of patients who continued to stage-II (monotherapy).

The results for patients who entered Stage-II are summarized in FIG. 2.

Discussion and Conclusion

The randomized phase-II trial of recurrent squamous-cell carcinoma of the head and neck showed a significant increase in progression free survival with addition of NRC-2694-A to paclitaxel and cisplatin/carboplatin chemotherapy. Resistance to cisplatin in cancer treatment is determined by over expression of EGFR tyrosine kinase receptors and suppress the cell death by antiapoptotic proteins upregulation in poor outcome patients who are treated with neoadjuvant cisplatin treatment. The phenomenon of multidrug resistance (MDR) during chemotherapy is one of the reasons for the limited clinical efficacy of chemotherapy agents. Importantly, overexpression of the epidermal growth factor receptor (EGFR) or any of its linked pathways occurs in more than 90% of head and neck cancers. Increased EGFR protein expression or EGFR gene copy number amplification are associated with poor prognosis, radiation-resistance, locoregional treatment failure, and increased rates of distant metastases. One of the reasons for the overexpression of EGFR could be due to radiation therapy, which is the standard line of treatment for head and neck cancers and such overexpression further resulting in disease recurrence.

The phase-III clinical trial of Pembrolizumab in R/M HNSCC, KEYNOTE-048, demonstrated ORR of 36% with combination of Pembrolizumab and platinum-based chemotherapy compared to 26% with Pembrolizumab alone in CPS>20 population (Burtness et al, The Lancet, 2019; 394 (10212): 1915-1928). Also, platinum-based chemotherapy alone without targeted therapy showed response of only 19.5%. In the same study, cetuximab showed ORR of 35.6% when combined with platinum-based chemotherapy (Vermorken et al, New England Journal of Medicine, 2008; 359 (11): 1116-27).

In contrast, NRC-2694-A demonstrated better efficacy in terms of PFS and ORR. The addition of NRC-2694-A to chemotherapy was associated with significant increase in the median progression free survival by 3 months. The study demonstrated a statistically significant improvement in PFS. Also, NRC-2694-A, in combination with platinum-based chemotherapy, significantly increased ORR compared to chemotherapy alone and with a favorable safety profile. Patients who received NRC-2694-A as a monotherapy after completion of chemotherapy also demonstrated objective response. This finding is important, as these patients would otherwise have disease progression, if untreated. Hence, continuation of NRC-2694-A post-chemotherapy would keep the disease under control in patients who do not have other treatment options.

The response rate observed with NRC-2694-A is observed to be better than approved monoclonal antibodies viz. cetuximab and pembrolizumab. Importantly, all currently approved treatment options for R/M HNSCC are injectable products that require supervised drug administration in hospital setup. Moreover, there are no orally active treatment options approved for R/M HNSCC to date. NRC-2694-A is an orally active tyrosine kinase inhibitor for the treatment of R/M HNSCC.

In conclusion, NRC-2694-A not only improved progression free survival and objective response in combination with platinum-based chemotherapy, but also benefitted patients with recurrent squamous cell carcinoma of head and neck when given as a monotherapy. It is evident that NRC-2694-A could be an important therapeutic option in the recurrent and/or metastatic setting of head and neck cancer.

The invention claimed is:

1. A method for treating recurrent and/or metastatic squamous cell carcinoma of the head and neck in a patient, the method comprising administering a compound to the patient, wherein the compound is (3-ethynyl-phenyl)-[7-methoxy-6-(3-morpholin-4-yl-propoxy)-quinazolin-4-yl]-amine (NRC-2694) or a pharmaceutically acceptable salt thereof.

2. The method according to claim 1, wherein the recurrent and/or metastatic squamous cell carcinoma of the head and neck is recurrent squamous cell carcinoma of the head and neck.

3. The method according to claim 1, wherein treating recurrent and/or metastatic squamous cell carcinoma of the head and neck comprises reducing the size of a tumour associated with the recurrent and/or metastatic squamous cell carcinoma of the head and neck.

4. The method according to claim 3, wherein the size of the tumour is reduced from base line by at least 10%, optionally wherein the size of the tumour is as measured in accordance with version 1.1 of the RECIST criteria.

5. The method according to claim 1, wherein the recurrent and/or metastatic squamous cell carcinoma of the head and neck is resistant to radiotherapy and/or chemotherapy.

6. A method for treating recurrent and/or metastatic head and neck cancer in a patient, the method comprising administering a compound to the patient, wherein:

the compound is (3-ethynyl-phenyl)-[7-methoxy-6-(3-morpholin-4-yl-propoxy)-quinazolin-4-yl]-amine (NRC-2694) or a pharmaceutically acceptable salt thereof; and treating the head and neck cancer comprises reducing the size of one or more tumours associated with the head and neck cancer.

7. The method according to claim 6, wherein the head and neck cancer is recurrent head and neck cancer.

8. The method according to claim 6, wherein the head and neck cancer is metastatic.

9. The method according to claim 6, wherein the head and neck cancer is squamous cell carcinoma of the head and neck.

10. The method according to claim 6, wherein the size of the tumour is reduced from base line by at least 10%, optionally wherein the size of the tumour is as measured in accordance with version 1.1 of the RECIST criteria.

11. The method according to claim 6, wherein the head and neck cancer is resistant to radiotherapy and/or chemotherapy.

12. The method according to claim 1 or claim 6, wherein the patient has received at least one line of cancer therapy prior to treatment with the compound.

13. The method according to claim 1 or claim 6, wherein the patient is a human patient.

14. The method according to claim 1 or claim 6, wherein the age of the patient is from 18 to 90 years.

15. The method according to claim 1 or claim 6, wherein the compound is NRC-2694 dihydrochloride or NRC-2694 monohydrochloride.

16. The method according to claim 1 or claim 6, wherein the compound is administered to the patient orally.

17. The method according to claim 1 or claim 6, wherein the compound is administered to the patient once or twice daily.

18. The method according to claim 1 or claim 6, wherein the compound is administered to the patient in a dose of from 50 mg/day to 500 mg/day.

19. The method according to claim 1 or claim 6, wherein the compound is for use in combination with (a) cisplatin and paclitaxel or (b) carboplatin and paclitaxel.

20. A method for treating recurrent squamous cell carcinoma of the head and neck in a patient, the method comprising administering a compound to the patient, which compound is (3-ethynyl-phenyl)-[7-methoxy-6-(3-morpholin-4-yl-propoxy)-quinazolin-4-yl]-amine (NRC-2694) or a pharmaceutically acceptable salt thereof.

21. The method of claim 2, wherein the recurrent and/or metastatic squamous cell carcinoma of the head and neck is metastatic recurrent squamous cell carcinoma of the head and neck.

22. The method of claim 12, wherein the patient has received at least two lines of cancer therapy prior to treatment with the compound.

23. The method of claim 14, wherein the age of the patient is 30 to 70 years.

24. The method of claim 15, wherein the compound is NRC-2694 dihydrochloride.

25. The method of claim 16, wherein the compound is administered to the patient in the form of a tablet or a capsule.

26. The method of claim 17, wherein the compound is administered to the patient once daily.

27. The method of claim 18, wherein the compound is administered to the patient in a dose of from 100 mg/day to 400 mg/day.

* * * * *